United States Patent
Nishiki et al.

(10) Patent No.: US 8,153,060 B2
(45) Date of Patent: Apr. 10, 2012

(54) AUTOMATIC ANALYZER

(75) Inventors: Kenichiro Nishiki, Hitachinaka (JP); Hajime Yamazaki, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 172 days.

(21) Appl. No.: 12/200,261

(22) Filed: Aug. 28, 2008

(65) Prior Publication Data

US 2009/0060792 A1 Mar. 5, 2009

(30) Foreign Application Priority Data

Aug. 31, 2007 (JP) ................................. 2007-224994

(51) Int. Cl.
*C12Q 1/68* (2006.01)

(52) U.S. Cl. ........... 422/50; 422/500; 422/415; 210/695
(58) Field of Classification Search ............ 422/99–101, 422/500–501, 50, 415; 210/695
See application file for complete search history.

(56) References Cited

U.S. PATENT DOCUMENTS

| | | | | | |
|---|---|---|---|---|---|
| 5,705,062 | A | * | 1/1998 | Knobel | 210/205 |
| 6,033,574 | A | * | 3/2000 | Siddiqi | 210/695 |
| 6,150,182 | A | | 11/2000 | Cassaday | |

FOREIGN PATENT DOCUMENTS

| | | |
|---|---|---|
| JP | 5-302930 A | 11/1993 |
| JP | 6-505673 | 6/1994 |
| JP | 8-43400 | 2/1996 |
| JP | 11-500952 A | 1/1999 |
| JP | 2003-144973 A | 5/2003 |

* cited by examiner

*Primary Examiner* — Jyoti Nagpaul
(74) *Attorney, Agent, or Firm* — Mattingly & Malur, PC

(57) ABSTRACT

An automatic analyzer includes a B/F separator including a reaction vessel holding unit provided with magnets disposed around a reaction vessel held on the reaction vessel holding unit and a rotating device for rotating the reaction vessel holding unit holding the reaction vessel about an axis of rotation aligned with the center axis of the reaction vessel or an axis of rotation parallel to and separated by a distance from the center axis of the reaction vessel. Both magnetic force and centrifugal force are exerted simultaneously on a specimen contained in a reaction vessel to capture magnetic particles contained in the liquid contained in the reaction vessel at a high capturing efficiency.

6 Claims, 10 Drawing Sheets

AXIS OF ROTATION    CENTER OF MAGNETIC FIELD

FIG. 10

CURVE A: VARIATION OF MAGNETIC FORCE WITH DISTANCE FROM THE CENTER AXIS OF THE REACTION VESSEL
CURVE B: VARIATION OF CENTRIFUGAL FORCE WITH DISTANCE FROM THE CENTER AXIS OF THE REACTION VESSEL
CURVE C: VARIATION OF RESULTANT FORCE OF MAGNETIC FORCE AND CENTRIFUGAL FORCE WITH DISTANCE FROM THE CENTER AXIS OF THE REACTION VESSEL
CURVE D: VARIATION OF MAGNETIC FORCE WITH DISTANCE FROM THE CENTER AXIS OF THE SEPARATOR VESSEL IN THE B/F SEPARATOR SHOWN IN FIG. 7

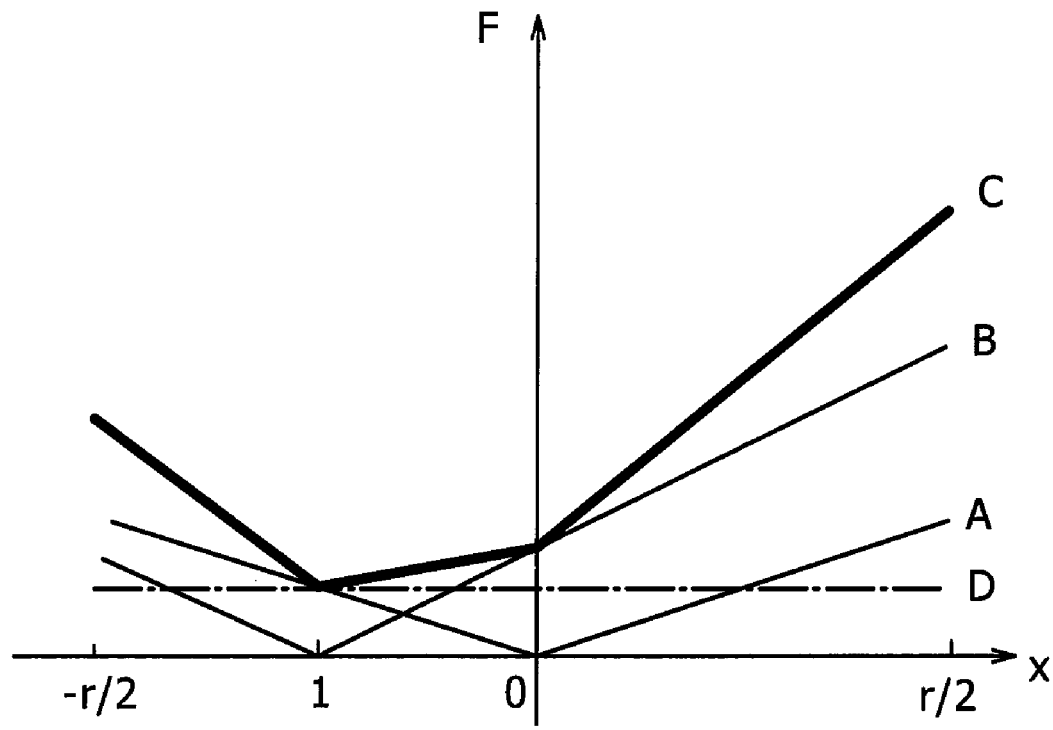

AUTOMATIC ANALYZER

BACKGROUND OF THE INVENTION

1. Field of the Invention

The present invention relates to an automatic analyzer for the qualitative and quantitative analysis of body fluids including serum and urine and, more particularly, to an automatic analyzer provided with a B/F separation mechanism (bound/free separation mechanism) for magnetically separating components idiosyncratically bonded to markers.

2. Description of the Related Art

Immunity measurement is the qualitative and quantitative determination of a specified antigen or antibody contained in a biological specimen, such as blood, urine or saliva. Usually, immunity measurement uses an antigen or an antibody suitable for measuring a measuring object and bonded to solid particles. The measuring object contained in the specimen is brought into contact with the antigen or antibody. Then, the measuring object labeled by an enzyme, namely, a labeled compound, is made to react with the antigen or antibody peculiarly reactive with the measuring object to bind the measuring object, and then the specimen is rinsed repeatedly to remove the unreacted enzyme-labeled antigen, namely, free antigen for bound/free separation (hereinafter, referred to as "B/F separation). Then, the labeled matter bonded to the measuring object of the specimen is measured to determine the quantity of the measuring object contained in the specimen.

Thus, immunity measurement requires troublesome operations for distribution, dilution, stirring, B/F separation and moving solid particles. Usually, the solid particles are polystyrene beads, magnetic particles or parts of the wall of a reaction vessel. Techniques and automatic analyzers using magnetic particles as solid particles for magnetic B/F separation have been developed, for example, an automatic analyzer proposed in, for example, JP-A-1996-043400 (Patent Document 1) is provided with a B/F separation mechanism.

The automatic analyzer proposed in JP-A-1996-043400 (Patent Document 1) uses magnetic particles as the solid particles to which a labeled substance is bonded, contains a liquid containing the labeled substance bonded to the magnetic particles in plural reaction vessels, and magnetically separates the solid particles from the liquid phase while the plural reaction vessels are moved on a processing line. Plural magnets are arranged along the processing line and apply a magnetic field to the liquid to move the reaction vessels at an increased moving speed.

[Patent Document 1] JP-A-1996-043400 [Patent Document 2] Japanese Translation of Unexamined PCT Application No. 1994-505673

B/F separation is used mainly by an automatic immunity analyzer. Therefore, BF separation is required to achieve high-speed separation and capturing at high capturing efficiency from the viewpoint of rapid measurement and multiple-specimen processing. Since a limited space is available for installing the automatic analyzer in the examination room, the automatic analyzer is required to be capable of being installed in a small space.

When external force, such as centrifugal force, inertial force or magnetic force, is used, for capturing the solid particles for B/F separation, there is a limit to the capturing efficiency. Capturing efficiency is a value obtained by dividing the number of the solid particles captured by B/F separation by the number of the solid particles contained in the solution before B/F separation and the separating time for which B/F separation is continued. The higher the capturing efficiency, the greater the number of the captured solid particles captured in a shorter time.

When a turntable and magnetic force are used for B/F separation as mentioned in JP-A 1996-043400 (Patent Document 1), magnets can be placed only on the outer side surface and the inside surface.

SUMMARY OF THE INVENTION

Accordingly, it is an object of the present invention to provide an automatic analyzer provided with a B/F separator capable of carrying out a separating operation at high separating efficiency, requiring a small space for installation, and capable of achieving high-speed separation.

The present invention provides an automatic analyzer provided with a B/F separator including: magnets that create magnetic fields, and a rotary mechanism for applying centrifugal force to reaction vessels; wherein the magnetic field and the centrifugal force are applied simultaneously to the reaction vessels.

In the automatic analyzer according to the present invention, the magnetic field and the centrifugal force may be applied to the reaction vessels individually to form the B/F separator in a small size.

In the automatic analyzer according to the present invention, each of the reaction vessels may be surrounded by a magnet to enhance capturing efficiency.

In the automatic analyzer according to the present invention, the axis of rotation may be separated from the center of the magnetic field such that centrifugal force can act on magnetic particles around the center of the magnetic field.

In the automatic analyzer according to the present invention, the magnets may respectively create magnetic fields of different magnitudes to separate the axis of rotation from the center of the magnetic field such that the respective centers of the centrifugal force and the magnetic field are separated.

In the automatic analyzer according to the present invention, the open upper end of the reaction vessel may be covered with a lid to prevent splashing about the solution when the reaction vessel is rotated at a high rotating speed.

Capturing efficiency can be improved by using both a magnetic field and centrifugal force for B/F separation and, consequently, analysis time can be reduced. Since the magnets can be arranged around each reaction vessel, a high capturing efficiency can be achieved. As compared with an automatic analyzer using a turntable, the automatic analyzer according to the present invention can achieve a high capturing efficiency because each reaction vessel is surrounded by magnets, and can be formed in a small size because the reaction vessels are rotated individually.

BRIEF DESCRIPTION OF THE DRAWINGS

FIG. 10 is a graph for assistance in explaining the effect of simultaneous exertion of magnetic force and centrifugal force on a specimen.

DESCRIPTION OF THE PREFERRED EMBODIMENTS

The object of providing an automatic analyzer provided with a B/F separator capable of operating at a separating efficiency higher than that of the conventional B/F separator and of high-speed separation and requiring a reduced space for installation can be achieved by the smallest possible number of parts.

Figure 6:
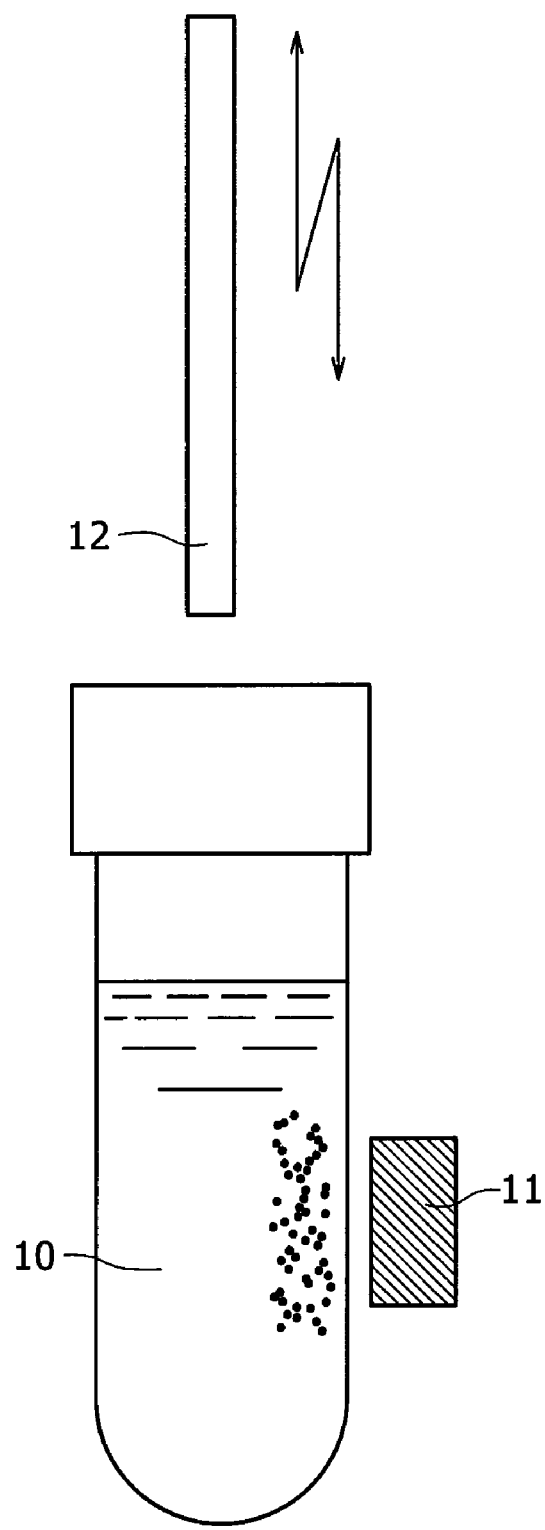
FIG. 6 is a view for assistance in explaining magnetic B/F separation.

FIG. 6 shows a magnetic B/F separator. A solution containing magnetic particles is poured into a separator vessel 10. Then, a magnet 11 is disposed beside the side wall of the separator vessel 10 to exert magnetic attraction on the magnetic particles by applying a magnetic field to the magnetic particles. The magnetized magnetic particles are magnetically attracted to the side wall of the separator vessel 10. Subsequently, a nozzle 12 for discharging and sucking water is inserted into the separator vessel 10. The solution containing free antigens or antibodies is sucked through the nozzle 12 to remove the same from the separator vessel 10, and then a new solution is discharged through the nozzle 12 into the separator vessel 12 to achieve B/F separation.

Figure 7A:
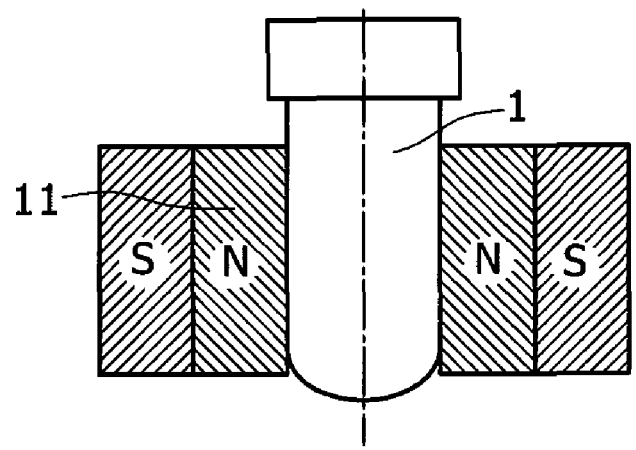
FIGS. 7A-7B are views for assistance in explaining the arrangement of magnets proposed in Jpn. Pat. App. No. 1992-506439 (Patent Document 2)
Figure 7B:
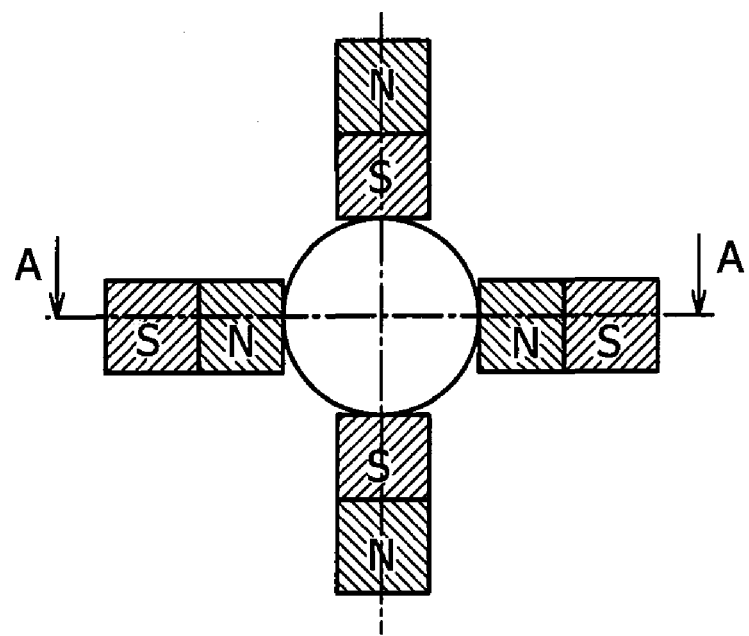

The B/F separator included in the automatic analyzer proposed in Jpn. Pat. App. No. 1992-506439 (corresponding to Patent Document 2: Unexamined PCT Application No. 1994-505673) subjects measuring objects individually to B/F separation without using any turntable. Magnets 11 are arranged as shown in FIGS. 7A-7B so that a gradient of magnetic flux density (hereinafter, referred to as "magnetic gradient") is created around the center axis of a separator vessel 1 to collect sold particles around the center axis.

The magnetic attraction acting on the magnetic particles is proportional to the magnetic flux density and the magnetic gradient. Since the magnetic flux density is fixed when the magnets are not changed, the magnitude of the magnetic attraction is greater when the magnetic gradient is higher.

Figure 8:
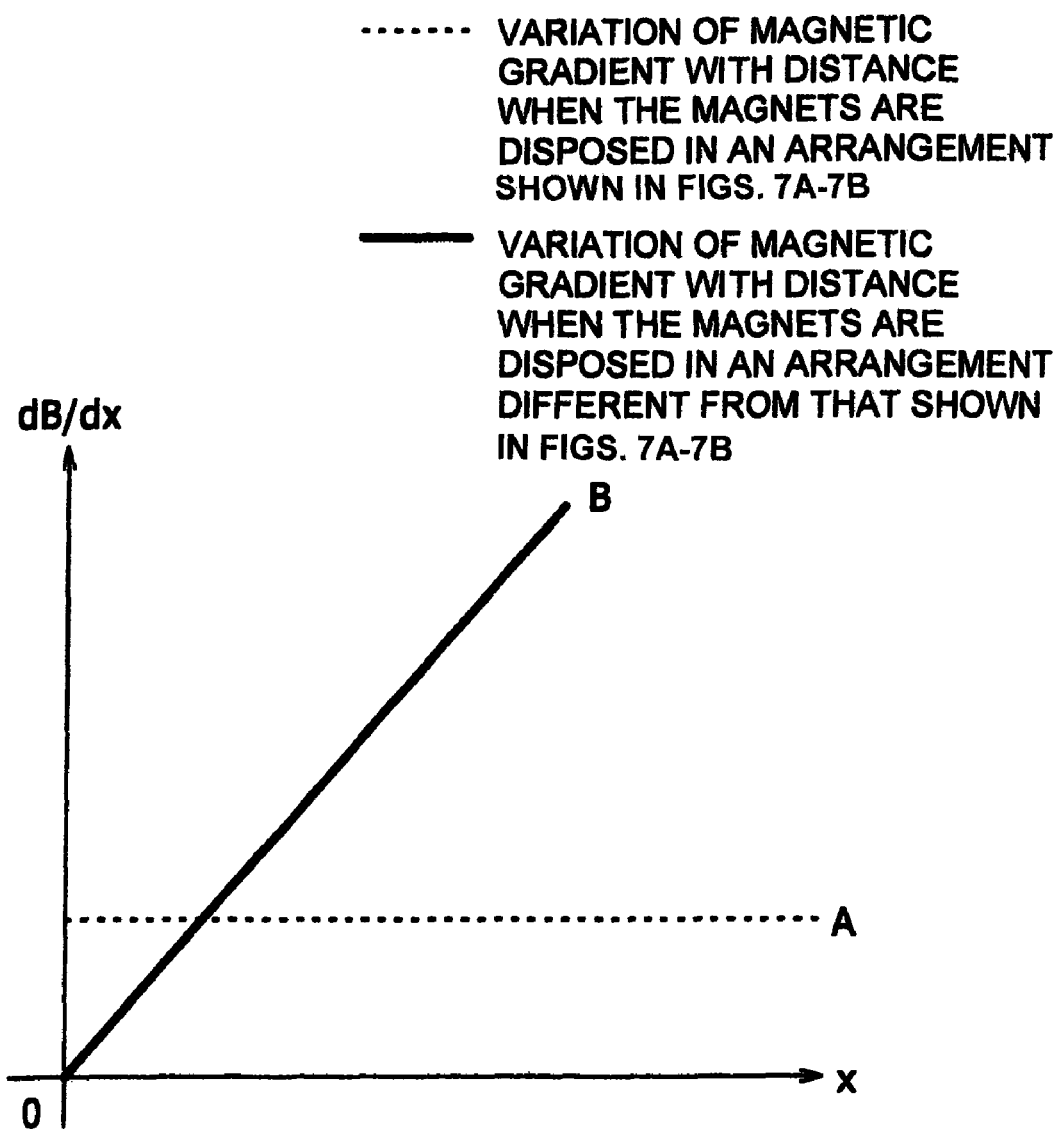
FIG. 8 is a graph showing the relation between the gradient of magnetic field intensity and distance when magnets are arranged as shown in FIGS. 7A-7B.

FIG. 8 shows the relation between magnetic gradient and distance. In FIG. 8, line A indicates the variation of magnetic gradient with distance from the center axis of the separator vessel when the magnets are disposed in an arrangement shown in FIGS. 7A-7B, and line B indicates the variation of magnetic gradient with distance from the center axis of the separator vessel when the magnets are disposed in an arrangement different from that shown in FIGS. 7A-7B. Line A indicates that magnetic gradient remains constant regardless of distance from the center axis of the separator vessel. Line B indicates that magnetic gradient is a linear function of distance from the center axis of the separator vessel, the intensity of the magnetic field at the center of the separator vessel is zero, and the intensity of the magnetic field at the longest distance from the center axis of the separator vessel is high. It is known from comparative examination of lines A and B shown in FIG. 8 that the magnetic particles can be efficiently captured by applying centrifugal force to the magnetic particles in the central part of the separator vessel in addition to magnetic attraction.

Figure 9A:
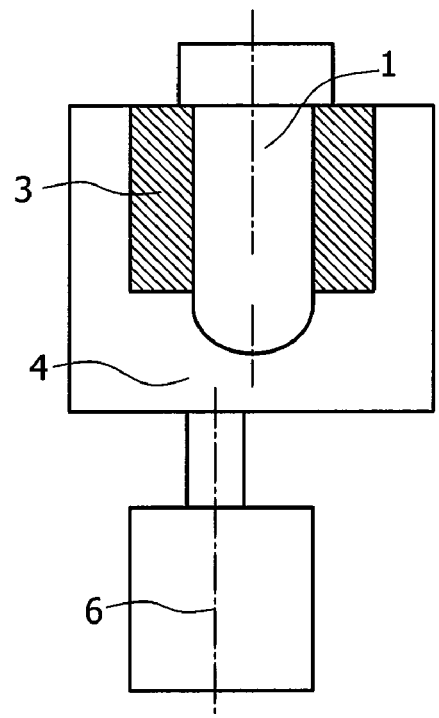
FIGS. 9A-9B are views for assistance in explaining a B/F separator in a modification of the B/F separator shown in FIG. 1.
Figure 9B:
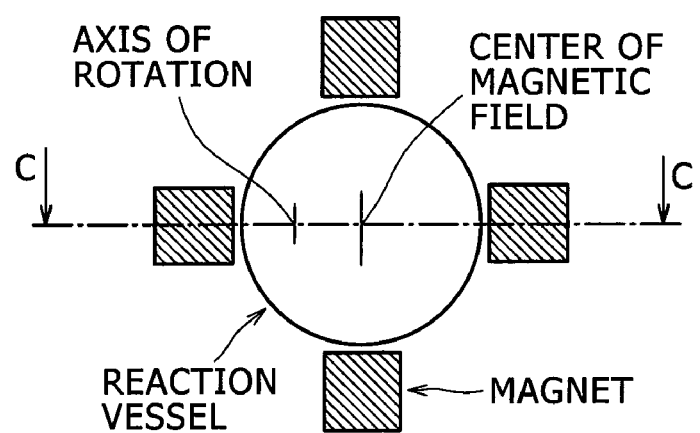
Figure 9B:
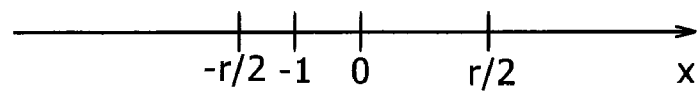

In FIGS. 9A-9B, the center axis of a magnetic field is not aligned with the axis of rotation of a separator vessel 1. External force acting on magnetic particles in a section taken on the line C-C in FIGS. 9A-9B is estimated on the assumption that the vessel 1 has an inside diameter r, and the axis of rotation of a motor 6 is separated from the center axis of the vessel 1 by a distance 1.

Magnetic force is proportional to magnetic gradient. The magnetic force varies as indicated by curve A shown in FIG. 10.

Centrifugal force is proportional to the distance from the axis of rotation. Since the axis of rotation of the motor 6 is at the distance 1 from the center of magnetic force (X=0), centrifugal force varies with distance from the center axis of the separator vessel as indicated by curve B in FIG. 10.

When both centrifugal force and magnetic force act on the magnetic particles, the resultant force of the centrifugal force and the magnetic force acts on the magnetic particles. Since the respective directions of action of the centrifugal force and the magnetic force are the same, the resultant force varies with distance from the center axis of the separator vessel as indicated by curve C in FIG. 10.

It is known from comparative examination of the curves A to D shown in FIG. 10 that a high force can be exerted on the magnetic particles when the magnetic force and the centrifugal force act simultaneously on the magnetic particles and, consequently, the magnetic particles can be efficiently captured.

This method of separating magnetic particles uses magnetic force. Another method uses centrifugal force and inertial force. For example, a method mentioned in Jpn. Pat. App. No. 1992-506439 (corresponding to Patent Document 2: Unexamined PCT Application No. 1994-505673) contains a liquid containing a target substance reacted with an antigen in a reaction vessel held on a turntable, and rotates the turntable to separate the solid phase from the liquid phase by applying centrifugal force to the liquid. Whereas this method rotates the turntable, a method according to the present invention rotates the reaction vessel to exert centrifugal force on the contents of the reaction vessel. Therefore, an automatic analyzer according to the present invention can be formed in a small size.

A preferred embodiment of the present invention will be described with reference to the accompanying drawings.

Figure 1:
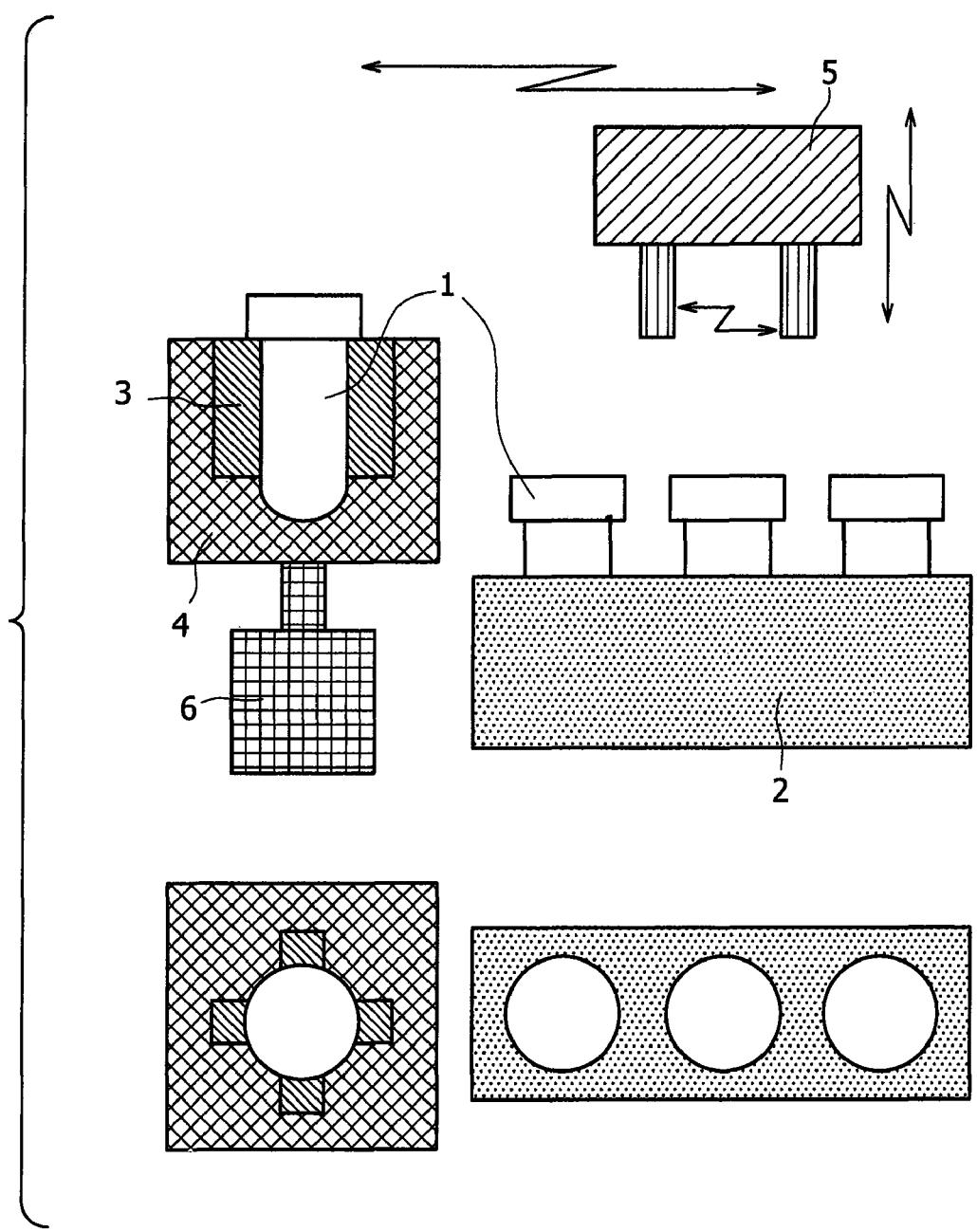
FIG. 1 is a view of a B/F separator included in an automatic analyzer in a preferred embodiment according to the present invention.

FIG. 1 shows a B/F separator included in an automatic analyzer in the preferred embodiment. The B/F separator includes a reaction vessel 1 for containing a reaction liquid, a reaction vessel storage unit 2, magnets 3 for capturing magnetic particles, a reaction vessel holding unit 4, and a motor for rotating the reaction vessel 6.

The reaction vessel 1 can contain about 200 ml of the reaction liquid and has the shape of a cylinder having an inside diameter of 6 mm and a length of about 30 mm.

The reaction vessel storage unit 2 needs to keep the reaction vessels at a fixed temperature to promote a reaction in the reaction vessels 1. When the reaction vessel storage unit 2 is expected to store thirty-two reaction vessels 1, the reaction vessel storage unit 2 is about 80 mm in width (W), about 50 mm in depth (D) and about 50 mm in height (H).

The magnets 3 are neodymium alloy magnets of about 6 mm in W, about 6 mm in D and about 10 mm in H.

The reaction vessel holding unit 4 holds the reaction vessel 1 and the magnets 3 are embedded therein. The reaction vessel holding unit 4 is about 40 mm in W, about 40 mm in D and about 40 mm in H. Since the reaction vessel holding unit 4 is rotated by the motor 6, the same may have a cylindrical shape.

A reaction vessel carrying mechanism 5 is about 100 mm in W, about 150 mm in D and about 50 mm in H.

The motor 6 needs to rotate the reaction vessel holding unit 4 at a rotating speed in the range of 101 to 109 rps. Since the object to be rotated by the motor 6 has a small mass and a small size, the motor 6 does not need to exert a high torque. The motor 6 is about 42 mm in W, about 42 mm in D and about 50 mm in H.

The sealed reaction vessel 1 containing a solution is carried from the reaction vessel storage unit 2 to and is held on the reaction vessel holding unit 4 provided with the magnets 3. The reaction vessel holding unit 4 holding the reaction vessel 1 is rotated by the motor 6. Then, magnetic particles contained in the reaction vessel 1 are collected on the side wall of the reaction vessel 1 by the agency of both the magnetic force exerted thereon by the magnets 6 and centrifugal force acting thereon when the reaction vessel holding unit 4 is rotated by the motor 6. Thus the magnetic particles are separated from the liquid phase of the solution. The solution may be poured into and sealed in a reaction vessel 1 after holding the empty reaction vessel 1 by the reaction vessel holding unit 4.

After the magnetic particles have been thus separated from the liquid phase of the solution, a nozzle for discharging and sucking water is inserted into the reaction vessel 1. The solution containing free antigens or antibodies is sucked through the nozzle to remove the same from the reaction vessel 1. The magnetic particles collected on the side wall of the reaction vessel are held on the side wall of the reaction vessel 1 only by magnetic attraction. Therefore, any problems will not arise even if the rotation of the reaction vessel 1 is stopped. When the centrifugal force is removed, the stirred surface of the solution calms down and hence the solution can be stably sucked out through the nozzle. Then, the magnetic particles are rinsed by discharging a new cleaning liquid through the nozzle into the reaction vessel to complete B/F separation.

Figure 2A:
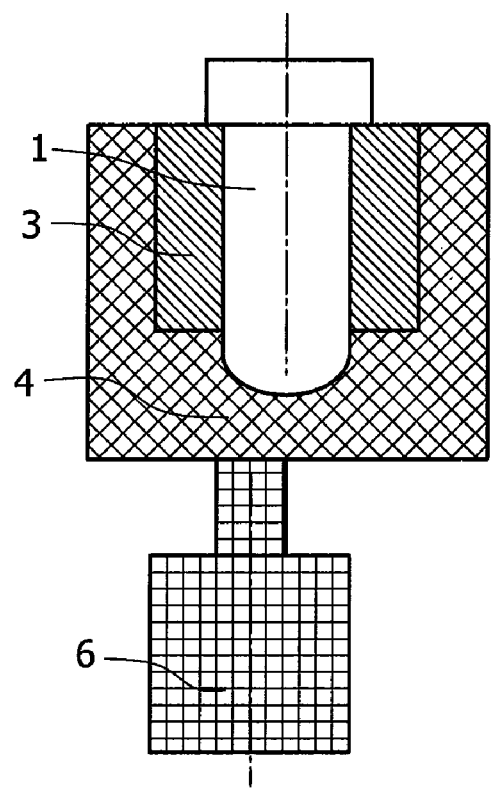
FIGS. 2A-2B are views of a B/F separator included in an automatic analyzer in a second embodiment according to the present invention.
Figure 2B:
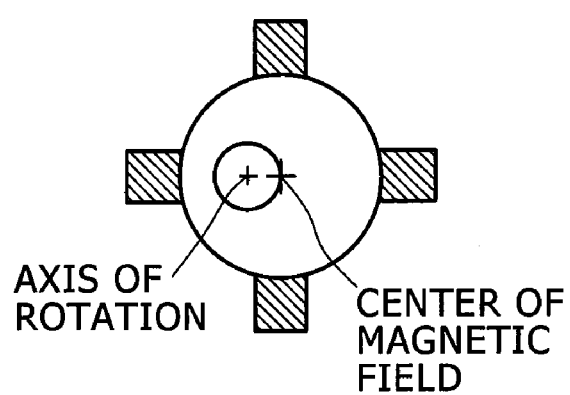

When the magnetic forces respectively exerted by the magnets disposed around the reaction vessel 1 are equal, a magnetic field created around the reaction vessel 1 has a magnetic gradient as indicated by line B shown in FIG. 8, and the magnetic force in the vicinity of the center axis of the reaction vessel 1 is substantially zero. The centrifugal force acting on the solution in the vicinity of the center axis of the reaction vessel 1 is substantially zero. Therefore, the B/F separator shown in FIG. 1 cannot capture the magnetic particles staying in the vicinity of the center axis of the reaction vessel 1. In a B/F separator shown in FIGS. 2A-2B, a reaction vessel holding unit 4 and a motor 6 are disposed such that the center axis of the motor 6 is separated a distance apart from the center axis of a reaction vessel 1 held by the reaction vessel holding unit 4. Thus, either of centrifugal force or magnetic force acts necessarily on magnetic particles contained in the reaction vessel 1. Centrifugal force acts on magnetic particles around the center axis of the reaction vessel 1, and magnetic force acts on magnetic particles in a part of the reaction vessel 1 aligned with the axis of rotation. Thus all the magnetic particles contained in the solution can be captured.

Figure 3A:
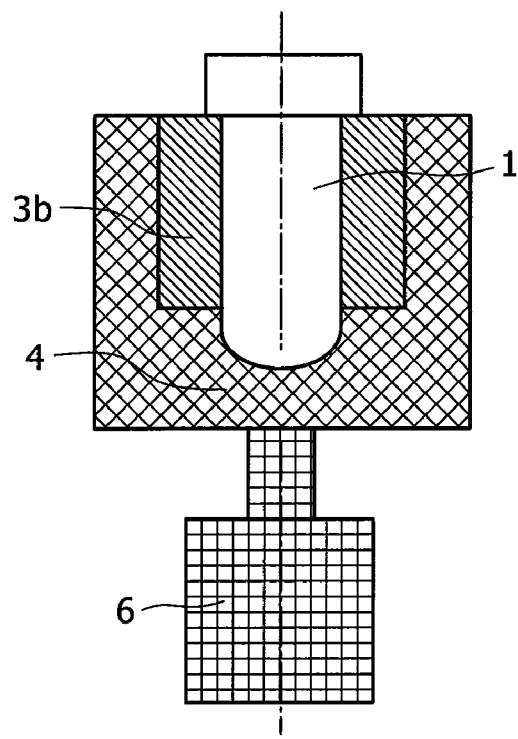
FIGS. 3A-3B are views of a B/F separator included in an automatic analyzer in a third embodiment according to the present invention.
Figure 3B:
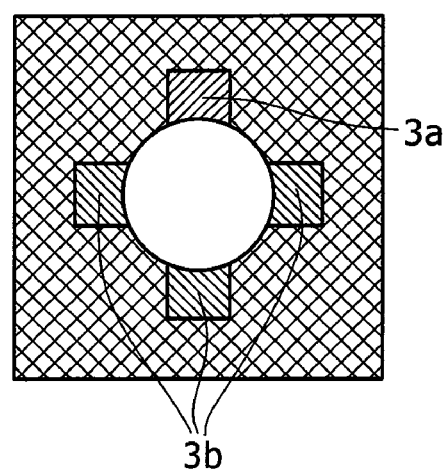

The same effect as mentioned above can be exercised by using magnets 3a and 3b respectively capable of creating magnetic fields of different intensities as shown in FIGS. 3A-3B. In FIGS. 3A-3B, the center of a composite magnetic field formed by the magnets 3a and 3b is separated from the axis of rotation of the motor.

Figure 4A:
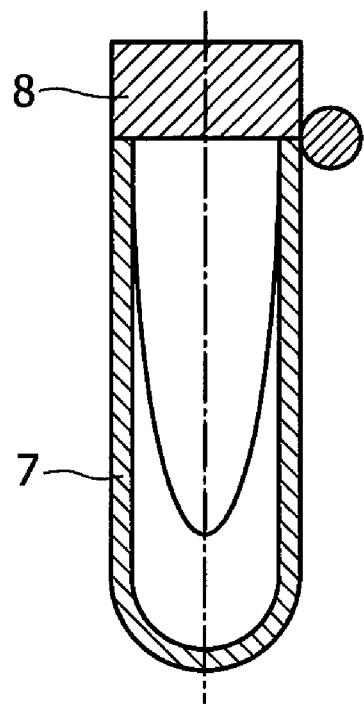
FIGS. 4A-4B are views of a reaction vessel suitable for use in combination with a B/F separator according to the present invention.
Figure 4B:
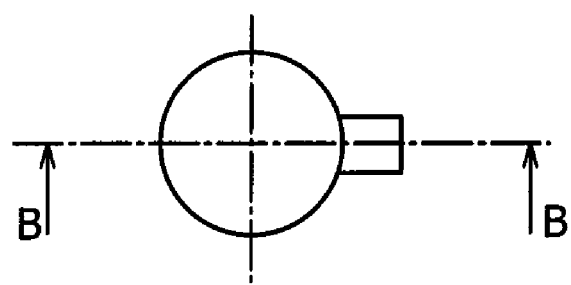

The reaction vessel 7 may be provided with a lid 8 as shown in FIGS. 4A-4B to prevent splashing about the solution when the reaction vessel 7 is rotated at a high rotating speed. Consequently, the magnetic particles can be more effectively captured.

Figure 5A:
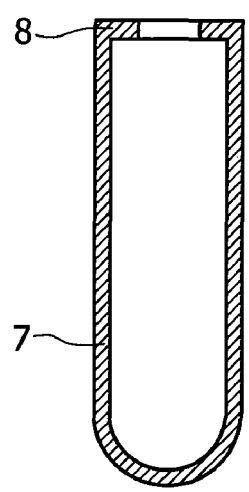
FIGS. 5A-5C are views of a reaction vessel suitable for use in combination with a B/F separator according to the present invention.
Figure 5C:
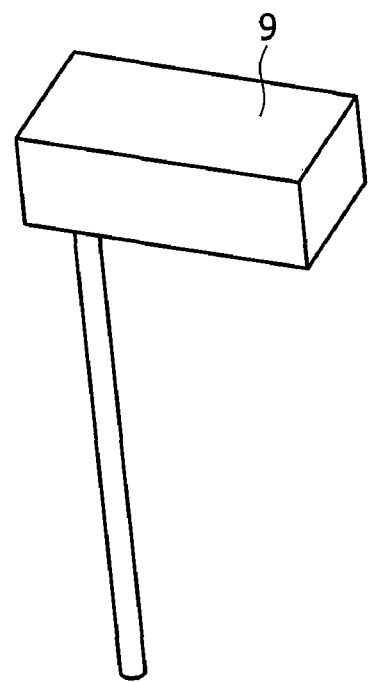
Figure 5B:
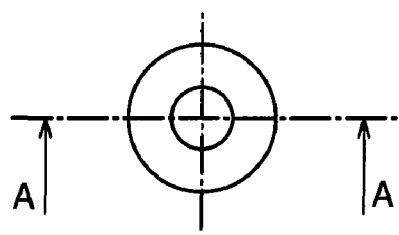
Figure 5B:
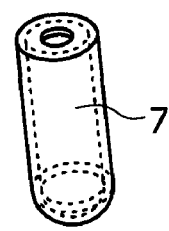

The lid 8 may be provided in its central part with an opening for receiving the nozzle 9 as shown in FIGS. 5A-5C. When centrifugal force is exerted on the liquid contained in the reaction vessel 7, the liquid is caused to move so that the surface of the liquid is formed in a shape as shown in FIGS. 4A-4B. Therefore, the liquid will not be splashed about through the opening of the lid.

What is claimed is:

1. An automatic analyzer comprising a B/F separator comprising:
   a reaction vessel for containing a specimen and a reagent;
   a reaction vessel holding unit provided with a plurality of magnetic force generating means for holding the reaction vessel and exerting a magnetic force on the specimen and the reagent contained in the reaction vessel; and
   a rotating means for rotating the reaction vessel holding unit around a center axis for exerting a centrifugal force on the specimen and the reagent contained in the reaction vessel;
   wherein the center axis of the rotating means is separated a distance apart from a center of a composite magnetic field formed by the magnetic force generating means.

2. The automatic analyzer according to claim 1,
   wherein a center axis of the reaction vessel is coincident with the center of the composite magnetic field and separated a distance apart from the center axis of the rotating means.

3. The automatic analyzer according to claim 1,
   wherein a center axis of the reaction vessel is coincident with the center axis of the rotating means and separated a distance apart from the center of the composite magnetic field.

4. An automatic analyzer comprising:
   a reaction vessel which holds a specimen and a reagent;
   a reaction vessel holding unit which holds the reaction vessel and is provided with a plurality of magnets to exert a magnetic force on the specimen and the reagent held in the reaction vessel; and
   a motor which rotates the reaction vessel holding unit around a center axis to exert a centrifugal force on the specimen and the reagent held in the reaction vessel;
   wherein the center axis of the motor is separated a distance apart from a center of a composite magnetic field formed by the magnets.

5. The automatic analyzer according to claim 4,
   wherein a center axis of the reaction vessel is coincident with the center of the composite magnetic field and separated a distance apart from the center axis of the motor.

6. The automatic analyzer according to claim 4,
   wherein a center axis of the reaction vessel is coincident with the center axis of the motor and separated a distance apart from the center of the composite magnetic field.

* * * * *